United States Patent [19]

Ridderheim et al.

[11] Patent Number: 4,955,870
[45] Date of Patent: Sep. 11, 1990

[54] HYPODERMIC SYRINGE WITH RETRACTABLE NEEDLE

[76] Inventors: Kristen A. Ridderheim, 8508 Gerig Rd., Leo, Ind. 46765; V. Widadi Sudharto, 6825-G Ramblewood Dr., Fort Wayne, Ind. 46835; Alice F. Ridderheim, 8508 Gerig Rd., Leo, Ind. 46765

[21] Appl. No.: 235,437

[22] Filed: Aug. 23, 1988

[51] Int. Cl.$^5$ .............................................. A61M 5/00
[52] U.S. Cl. .................................... 604/195; 604/198
[58] Field of Search ............... 604/195, 198, 194, 187, 604/228, 218, 136, 263

[56] References Cited

U.S. PATENT DOCUMENTS

2,722,215 11/1955 Dahlgren ......................... 604/228 X
4,874,382 10/1989 Lindemann et al. ................. 604/198

Primary Examiner—John D. Yasko
Attorney, Agent, or Firm—George Pappas

[57] ABSTRACT

A hypodermic syringe including a barrel having a closed end, an open end, and an interior surface. A plunger is reciprocally received in the barrel through the open end and in sealing engagement with the interior surface of the barrel and forming a chamber. A hollow needle is detachably attached to the barrel at the closed end of the barrel. The plunger has a hole leading to a cavity. A spring is located within the cavity and is connected to the plunger at one end and a first mating member at the other end. The first mating member is detachably attached to the plunger end. A second mating member is attached to the needle. In operation, liquid is injected in a normal fashion by pushing the plunger toward the closed end of the barrel. When the plunger approaches the barrel closed end, the first and second mating members attach to one another. Further forward movement of the plunger first detaches the needle from the barrel and, thereafter, detaches the second mating member from the plunger and, thus, the spring draws the needle through the hole to within the cavity.

33 Claims, 3 Drawing Sheets

HYPODERMIC SYRINGE WITH RETRACTABLE NEEDLE

BACKGROUND OF THE INVENTION

This invention relates generally to hypodermic syringes and seeks to solve the problem of accidental puncture with contaminated needles of hypodermic syringes. The hypodermic syringe, according to the present invention, is adapted so that after it is used and substantially at the end of the plunger stroke, the needle is detached from the syringe barrel and is retracted to within a cavity located in the plunger and out of one's way.

The problems associated with accidental puncture with contaminated hypodermic syringe needles has, in recent times, increased and has become substantially grave. Individuals in various health service organizations, such as nurses and doctors, that use hypodermic syringes, are increasingly under pressure to more quickly perform their duties and, thus, are less likely to be cautious when using hypodermic syringes and from potentially being punctured by a contaminated needle. Further, during emergency situations, it is quite often very difficult to be cautious so as to not be punctured by a contaminated needle. The probability of being punctured is further increased in emergency situations when a patient, for example, is convulsive.

The problem of being scratched or punctured has become yet more grave in view of the advent of the Acquired Immune Deficiency Syndrome (AIDS) spreading and becoming more common. As can be appreciated, a health service worker treating an AIDS patient or a patient having hepatitis, can easily contract either of those diseases should he or she be punctured or scratched by a contaminated needle. Accordingly, a need exists for a hypodermic syringe that retracts or hides a contaminated needle after use so that the user of the hypodermic syringe does not become punctured or scratched by the contaminated needle.

Furthermore, a problem exists in the spreading of AIDS among drug users and, thereafter, to the general population. This problem exists in that drug users tend to share and reuse hypodermic syringe needles thereby contracting AIDS or hepatitis from a contaminated needle previously used by someone affected by AIDS or hepatitis. In addition to the problem of accidental punctures and scratches, there is a need to limit or eliminate the reusability of hypodermic syringes or for making a hypodermic syringe unusable after the original and first use.

Various hypodermic syringes have been developed in the past for preventing accidental punctures and scratches by contaminated needles. For example, U.S. Pat. No. 4,026,287; U.S. Pat. No. 4,675,005; and, U.S. Pat. No. 4,692,156 disclose syringes whereby the needle is withdrawn to within the syringe barrel after use. These syringes include a plunger that attaches to the needle and, by pulling the plunger outwardly from within the syringe barrel, the contaminated needle is pulled into the syringe barrel and out of the user's way. As can be appreciated, these syringe devices are difficult to operate in that at the end of an injection, the user must use both hands to attach the plunger to the needle and, thereafter, withdraw the plunger back pulling the needle to within the syringe barrel. This is not only difficult but also time consuming and potentially impractical in today's health service organizations.

Other hypodermic syringe devices of the past, such as those disclosed in U.S. Pat. No. 4,664,654 and U.S. Pat. No. 4,702,738 utilize guards or sheaths for covering a contaminated needle after use. This, however, requires additional components to be carried on the syringe and also requires additional steps at the end of an injection so as to cover the contaminated needle.

Accordingly, a need exists for a hypodermic syringe that is substantially easy and inexpensive to manufacture and that does not require additional steps during use for the covering or retracting of the contaminated needle. A need exists for a hypodermic syringe that is used in the same fashion as other common hypodermic syringes and, that, automatically retracts and places the contaminated needle out of the way at the end of an injection and with minimal effort by the user. A need further exists for a hypodermic syringe that, upon the first use thereof, substantially renders itself unusable and, thereby, preventing the spread of diseases among drug users that share hypodermic syringe needles.

SUMMARY OF THE INVENTION

It is the principle object of the present invention to overcome the above-discussed disadvantages associated with prior art hypodermic syringes and to fill the needs associated therewith. It is further the object of this invention to provide a hypodermic syringe that causes a contaminated needle to be retracted out of the way with merely a regular stroke of the plunger within the syringe barrel substantially at the end of an injection.

The hypodermic syringe, according to the present invention, includes a barrel having a closed end, an open end, and an interior surface, and a hollow needle is detachably attached to the barrel at the closed end. A plunger is reciprocally received in the barrel through the open end and is in sealing engagement with the interior surface of the barrel. Thus, a liquid retention chamber is formed between the plunger and the interior surface of the barrel. Liquid therein is pressurized by the pushing of the plunger into the barrel and is, thus, also caused to exit from the chamber through the hollow needle. The plunger includes a hole leading into a cavity for receiving the needle therein when it is detached from the barrel. A biasing means or spring is provided within the cavity and is attached to the plunger. An attachment means is provided and is connected to the spring and causes the spring to be attached to the needle when the plunger approaches the barrel closed end. In this regard, the attachment means includes a first mating member connected to the spring and a second mating member connected to the needle, both of which are adapted to attach to one another when the plunger approaches the barrel closed end.

In operation, the plunger is pushed toward the barrel closed end thereby forcing the liquid within the chamber to be injected through the hollow needle in a normal fashion. Substantially toward the end of the injection stroke, the first and second mating members at first attach to one another. Slight further movement of the plunger toward the barrel closed end causes the hollow needle to be detached from the barrel. Thereafter, slight further movement of the plunger toward the barrel closed end causes the first mating member to be released from the forward portion of the plunger and causing the spring to draw or pull the first mating member along with the second mating member and the contaminated needle to within the cavity of the plunger. Accordingly, the contaminated needle is retracted out of the way substantially eliminating potential puncture or scratching thereby and all with merely a continuing forward stroke of the plunger within the barrel. Further, the hypodermic syringe is rendered unusable and the sharing and reusing thereof by drug users is substantially eliminated.

In one form thereof, the present invention relates to a hypodermic syringe including a barrel having a closed end, an open end, and an interior surface. A plunger is reciprocally received in the barrel through the open end and is in sealing engagement with the interior surface of the barrel and forming a chamber. A hollow needle is detachably attached to the barrel at the closed end and provides communication between the chamber and the exterior of the barrel so that liquid in the chamber may be injected. A hole is provided in the plunger for receiving the needle therethrough. A biasing means is connected to the plunger and is attachable to the needle. The biasing means draws the needle through the plunger hole when the needle is detached from the barrel.

In one form thereof, the present invention relates to a hypodermic syringe including a barrel having a closed end, an open end, and an interior surface. A plunger is reciprocally received in the barrel through the open end and is in sealing engagement with the interior surface of the barrel and forms a chamber therein. A hollow needle is detachably attached to the barrel at the closed end and provides communication between the chamber and the exterior of the barrel so that liquid in the chamber may be injected. A hole is provided in the plunger for receiving the needle therethrough and a cavity in the plunger communicates with the hole and receives the needle therein when detached from the barrel. A biasing means is connected to the plunger for drawing the needle through the plunger hole and into the cavity when the needle is detached from the barrel. An attachment means is connected to the biasing means and is located between the biasing means and the needle. The attachment means is provided for attaching the biasing means to the needle when the plunger approaches the barrel closed end.

BRIEF DESCRIPTION OF THE DRAWINGS

The above-mentioned and other features and objects of this invention and the manner of obtaining them will become more apparent and the invention itself will be better understood by reference to the following description of embodiments of the invention taken in conjunction with the accompanying drawings wherein.

Correspondence reference characters indicate correspondence parts throughout the several views of the drawings.

The exemplifications set out herein illustrate preferred embodiments of the invention in one form thereof and such exemplifications are not to be construed as limiting the scope of the disclosure or the scope of the invention in any manner.

DESCRIPTION OF SPECIFIC EMBODIMENTS

As shown in the drawings, a specific embodiment of the present invention is a hypodermic syringe generally indicated as 10. Hypodermic syringe 10 is adapted to retract or withdraw hollow needle 12 to within plunger 14 immediately after the syringe has been used so that the user cannot accidentally be scratched, punctured, or poked with the used hollow needle 12 which may, at that time, be contaminated.

Figures 1, 2, 3, 4:
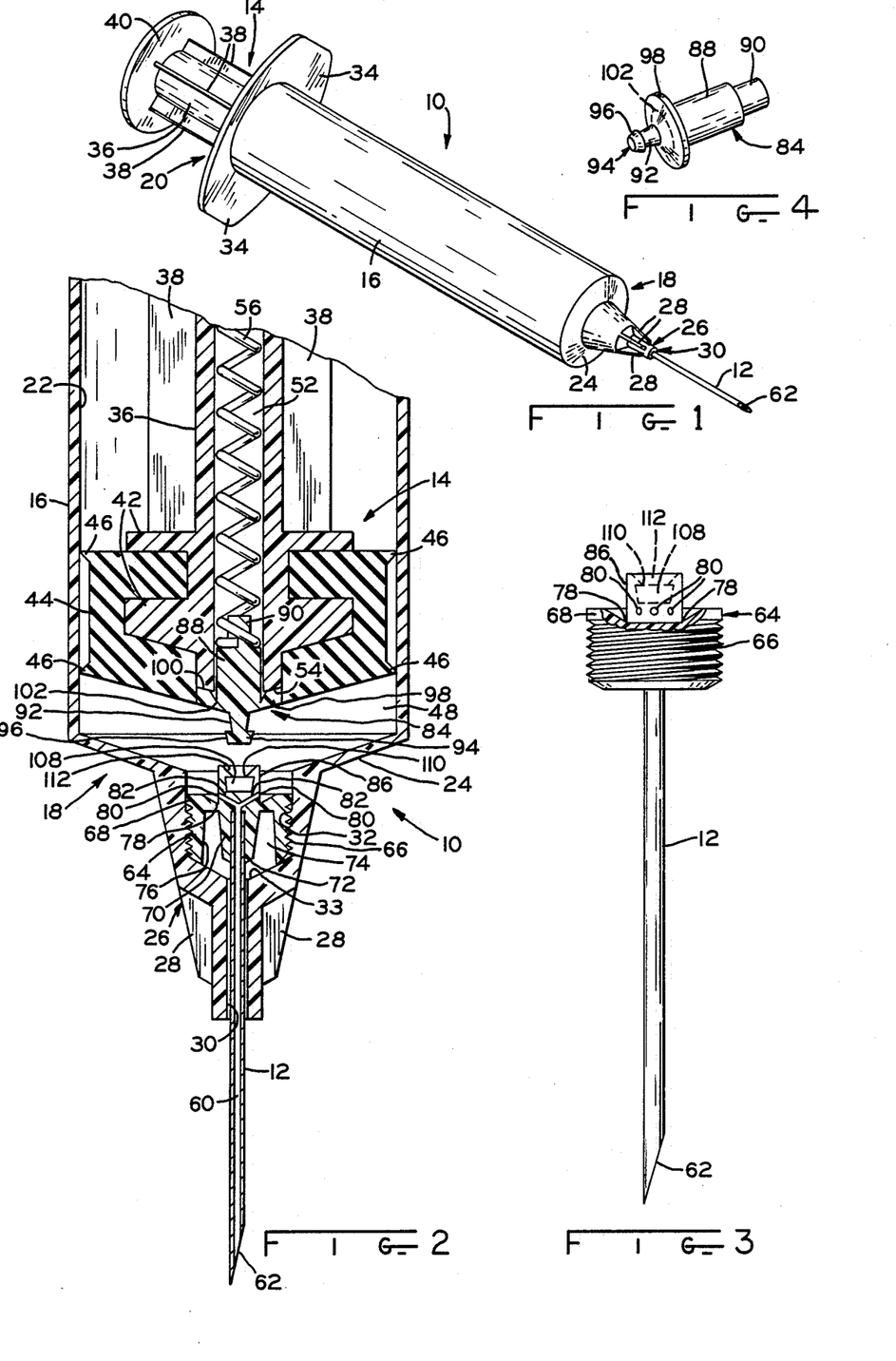
FIG. 1 is a perspective view of the hypodermic syringe according to the present invention.
FIG. 2 is a cross sectional partial elevational view of the forward portion of the hypodermic syringe of FIG. 1.
FIG. 3 is a side elevational view with a cut-away portion of the needle and plug of the hypodermic syringe of FIG. 2.
FIG. 4 is a perspective view of the first mating member of the hypodermic syringe of FIG. 2.

More specifically, hypodermic syringe 10 includes a barrel 16 having a closed end 18 and an open end 20. As shown in FIG. 2, barrel 16 has an interior surface 22 that is substantially smooth and also cylindrically shaped. Barrel 16 is closed at end 18 by barrel wall 24 which is frusto-conically shaped and integrally connected to barrel 16. Barrel wall 24 is also integrally connected to frusto-conical portion 26 which includes supporting ribs 28 and a needle receiving bore 30 communicating with a threaded bore 32. A seat 33 is substantially frusto-conically shaped and connects threaded bore 32 and needle receiving bore 30. As more fully described hereinbelow, needle receiving bore 30 and threaded bore 32 receive and support needle 12. At the open end 20 of barrel 16, ears 34 are integrally connected to barrel 16 and are provided for gripping and pushing plunger 14 within barrel 16 during operation.

Plunger 14 is reciprocally received in barrel 16 through open end 20. Plunger 14 includes cylindrical body 36 which is structurally reinforced with integral plunger ribs 38. At one end, plunger 14 has connected thereto thumb pad 40 which is substantially disk-shaped and upon which force is applied during operation, generally by the user's thumb. The other end of plunger 14 includes retaining rings 42. Rubber sealing member 44 fits snugly between and over retaining rings 42 and, thus, a seal is formed between plunger 14 and rubber sealing member 44 whereby liquid is prevented from seeping therebetween. Rubber sealing member 44 is sized so as to be in sealing engagement with the interior surface 22 of barrel 16. Rubber sealing member further includes rubber protruding rings 46 so as to provide a yet better sealing engagement and for more readily wiping and pushing fluid within barrel 16 toward closed end 18 of barrel 16. Accordingly, a liquid retention chamber 48 is formed when plunger 14 is received in open end 20 of barrel 16 between plunger 14 and rubber sealing member 44 and the interior surface 22 of barrel 16. When plunger 14 is within barrel 16 as shown in FIG. 2, liquid within retention chamber 48 may exit therefrom or be drawn into retention chamber 48 only through hollow needle 12, as more fully described hereinbelow.

Figures 5, 6, 7:
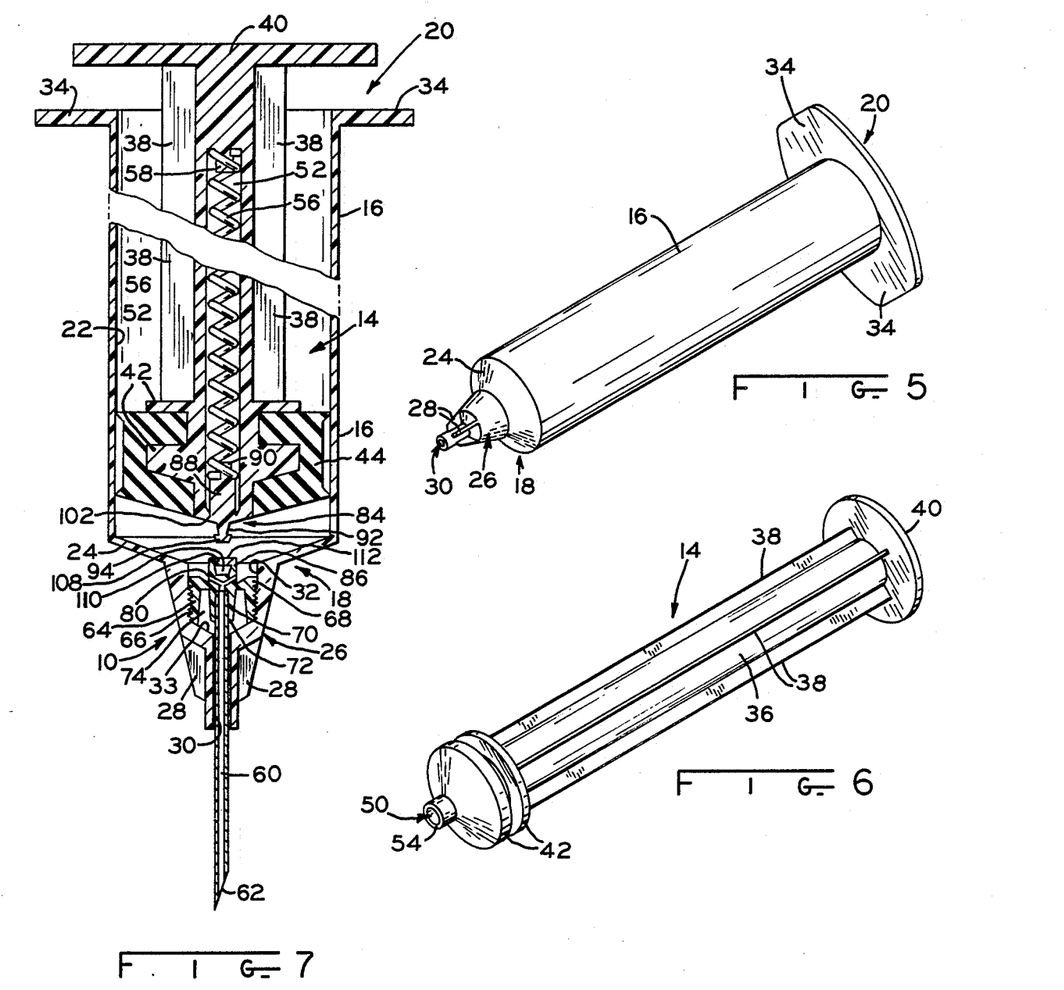
FIG. 5 is a perspective view of the barrel of the hypodermic syringe of claim 1.
FIG. 6 is a perspective view of the plunger of the hypodermic syringe of FIG. 1.
FIG. 7 is a cut-away side elevational view of a second embodiment of the hypodermic syringe of FIG. 1.

More clearly, as shown in FIG. 6, plunger 14 includes a hole 50 for receiving needle 12 therethrough and into plunger 14. More specifically, a cavity means or duct 52 extends within cylindrical body 36 of plunger 14 and communicates with plunger hole 50. Duct 52 is substantially cylindrically-shaped and has a smooth interior surface. Cavity means or duct 52 is adapted to receive needle 12 therein as shown in FIG. 9e. A seat 54 surrounds the opening of plunger hole 50.

A biasing means is located within duct 52 and is connected between the plunger 14 and is adapted for attachment to needle 12 so as to draw needle 12 through plunger hole 50 and into duct 52 when the needle 12 is detached from barrel 16. More specifically, the biasing means of the preferred embodiment is a helical spring located within duct 52 and connected at its upper end to extension 58 extending within duct 52 through the use of an adhesive or mechanical means. As can be appreciated, other biasing means such as rubber bands, etc., may also be used. Helical spring 56 at its lower other end is connected to an attachment means for attaching the biasing means or helical spring 56 to needle 12 at the end of the injection stroke of plunger 14 or when plunger 14 approaches the barrel closed end 18.

Needle 12 is hollow having a bore 60 therethrough and has a sharp end 62. Sharp end 62 is utilized in puncturing the skin of an animal or human followed by the insertion of hollow needle 12 in a known and customary manner. The upper part of needle 12 is connected to the attachment means for attachment to helical spring 56 when plunger 14 approaches barrel closed end 18. The upper part of needle 12 is also connected to a plug 64 having an outer threaded surface 66 and an upper ring portion 68. A sleeve 70 surrounds the upper portion of needle 12 and is rigidly attached thereto. Sleeve 70 includes a lower seat portion 72. An annular cavity 74 is, thus, formed between sleeve 70 and the inner surface 76 of plug 64. Sleeve 70, substantially at its upper end thereof, is detachably attached to plug 64 and, thus, because plug 64 is threadably attached to barrel 16, needle 12 is also detachably attached to barrel 16. More specifically, sleeve 70 is attached to plug 64 through a region of structural weakness 78 so that when a predetermined substantially longitudinal force is experienced by sleeve 70 and needle 12, sleeve 70 breaks away from plug 64 substantially at the region of structural weakness 78.

The upper portion of sleeve 70 includes holes 80 leading to and communicating with passageways 82 that, in turn, communicate with bore 60 of needle 12. Holes 80 are located above plug 64 and upper ring portion 68 and, thus, communicate with chamber 48. So as to increase the flow of fluid from within chamber 48 and out through needle 12, a plurality of passageways 82 are provided, all extending radially outwardly from the longitudinal axis of sleeve 70 and needle 12. All passageways 82, however, converge into and communicate with bore 60 of needle 12.

The attachment means includes a first mating member 84 connected to helical spring 56 and a second mating member 86 connected to needle 12 through sleeve 70. The first mating member 84 and second mating member 86 attach to one another when plunger 14 approaches the barrel closed end 18. It should also be noted that the mating members may be reversed so that the second mating member is attached to spring 56 and the first mating member is attached to needle 12.

As shown in FIG. 2 and FIG. 4, the first mating member 84 includes a rod portion 88 and an extension 90 is connected thereto and extends upwardly therefrom. Helical spring 56 is attached to extension 90 through the use of an adhesive or mechanical means. First mating member 84 at its lower end includes a protrusion 92 leading to and connected to an enlarged portion 94 which is shaped similar to a truncated thick rod having an outer wall 96 that is frusto-conically shaped. Enlarged portion 94 may also be substantially dome-shaped (not shown). First mating member 84 further includes a detachably attached annular lip 98 that is larger in diameter than the plunger hole 50 of plunger 14. Annular lip 98 has an upper seat portion 100. Annular lip 98 is attached to rod portion 88 through an area of structural weakness 102 so that predetermined substantially longitudinal force upwardly on first mating member 84 causes rod portion 88 to be detached or break away from annular lip 98 by the breaking away of annular lip 98 from rod 88 at the area of structural weakness 102. As more clearly shown in FIG. 2, the outer diameter of rod portion 88 is smaller than the inner diameter of duct 52 so that when rod 88 is detached from annular lip 98, helical spring 56 draws or pulls rod portion 88 upwardly and within duct 52. It should also be noted that, as shown in FIG. 2, seat 100 of annular lip 98 rests against seat 54 of plunger 14 creating a seal therebetween and preventing liquid within chamber 48, during the injection stroke, from entering duct 52. Furthermore, helical spring 56 provides the necessary force upwardly so as to retain annular lip 98 and plunger 14 in a seating and sealing arrangement.

In assembling the embodiment shown in FIG. 2, helical spring 56 is first inserted into duct 52 and attached to plunger 14 at extension 58 (FIG. 7). Thereafter, helical spring 56 is withdrawn from duct 52 and first mating member 84 is attached thereto. First mating member 84 is then placed in position as shown in FIG. 2 whereat first mating member is retained in that position through the upward provided force of helical spring 56.

In a second embodiment as shown in FIG. 7, first mating member 84 is integrally formed with plunger 14 and the area of structural weakness 102 is also integrally formed therewith. In this embodiment, the assembly of plunger 14 requires that access to duct 52 be provided from the upper portion of plunger 14 so that helical spring 56 is first attached to first mating member 84. Spring 56 is then withdrawn upwardly and out of duct 52 and is attached to extension 58 of plunger 14. Thereafter, spring 56 is placed in position and duct 52 is capped or closed through, for example, thumb pad 40. As in the first embodiment, a predetermined substantially longitudinal force upwardly on first mating member 84 causes the first mating member to break away from plunger 14 at the area of structural weakness 102 and, thus, first mating member 84 is thereafter withdrawn or pulled upwardly into duct 52.

Figure 8:
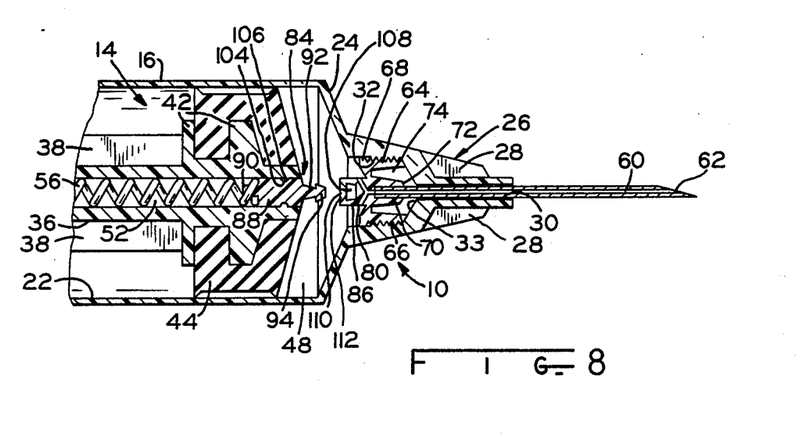
FIG. 8 is a cut-away side elevational view of a third embodiment of the hypodermic syringe of FIG. 1; and, FIGS. 9a–9e are cut-away elevational side views of the hypodermic syringe of FIG. 1 and showing the syringe in operation and retracting the needle into the plunger.

In a third embodiment, as shown in FIG. 8, the first mating member includes an annular groove 104 and receives an annular ring 106 that is connected to plunger 14 and extends into duct 52 and annular groove 104. As with the first embodiment shown in FIG. 2, ring 106 and groove 104 are in sealing engagement with one another and prevent liquid from entering duct 52 from chamber 48. Furthermore, a predetermined substantially longitudinal force forces ring 106 out of groove 104 thereby detaching first mating member 84 from plunger 14 and allowing spring 56 to draw or pull first mating member 84 to within duct 52.

The above-mentioned second mating member 86 of the attachment means is connected to needle 12 through sleeve 70. Second mating member 86 includes a bore 108 for receiving protrusion 92 and enlarged portion 94. Second mating member 86 further includes a catch means for catching and holding the protrusion 92 or enlarged portion 94 of the first mating member in the bore 108 when received therein. The catch means includes an annular lip 110 extending into bore 108 of the second mating member 86. Annular lip 110 includes an upper frusto-conical smooth wall 112 for aiding in receiving enlarged portion 94 within bore 108. Accordingly, when enlarged portion 94 of first mating member 84 is pushed against the second mating member 86, walls 112 and 96 mate causing annular lip 110 to enlarge in diameter and, thus, also cause enlarged portion 94 to be received within bore 108. Annular lip 110 is formed of a resilient material and, thus, substantially returns to its original smaller diameter after enlarged portion 94 is received within bore 108. Thus, enlarged portion 94 is securely and positively retained within bore 108.

The operation of the hypodermic syringe of a retractable needle is now described hereinbelow as also shown in FIGS. 9a–9e. In operation, the fluid to be injected is drawn or placed within chamber 48 in a known and customary manner, generally by drawing the liquid up through needle 12 and into chamber 48 by creating a vacuum within barrel 16 when plunger 14 is pulled outwardly therefrom. Thereafter, the needle 12 is inserted into an animal or a human and plunger 14 is pushed downwardly and within barrel 16 towards closed end 18. This causes the liquid within chamber 48 to be pressurized and, thus, the liquid is forced out of chamber 48 through holes 80, passageways 82 and bore 60 of needle 12 and into the animal or patient. Liquid within chamber 48 is prevented from seeping back behind plunger 14 as described hereinabove through the sealing engagement of rubber sealing member 44 with the interior surface 22 of barrel 16. Further, liquid within chamber 48 is prevented from seeping into duct 52 housing helical spring 56, through the seat formed between the annular lip 98 of first mating member 84 and plunger 14.

Figure 9A:
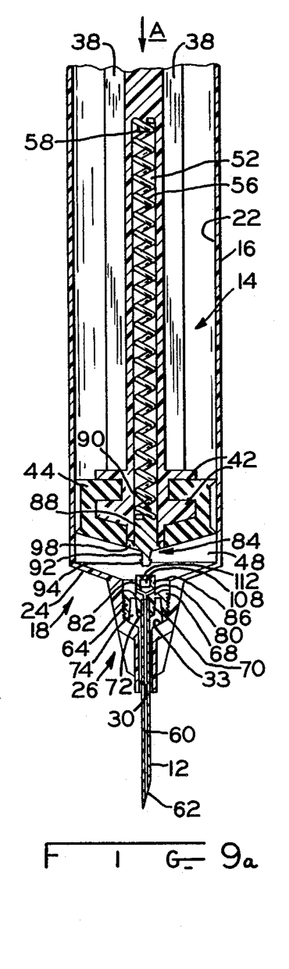
Figure 9B:
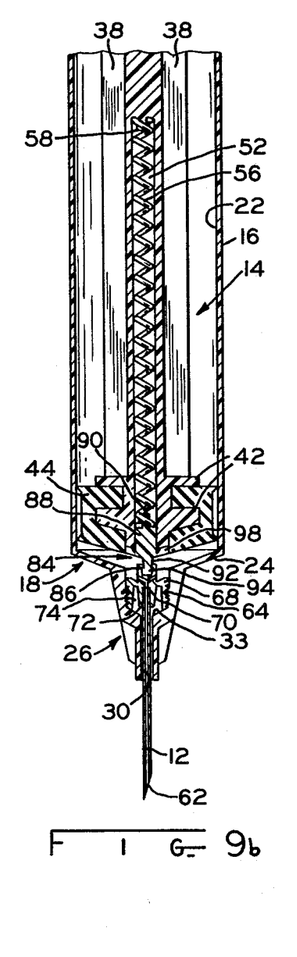

When plunger 14 reaches a predetermined distance, as shown in FIG. 9b, the attachment means causes spring 56 to be connected to needle 12. More specifically, the protrusion 92 and/or enlarged portion 94 are forced within bore 108, as shown, and are locked or retained therein through the catch means. As more fully described hereinabove, annular lip 110 is forced radially outwardly as enlarged portion 94 is forced longitudinally downwardly via walls 96 and 112 rubbing against one another. Thereafter, when enlarged portion 94 is within bore 108, annular lip 110 returns substantially to its original diameter enclosing and catching enlarged portion 94 within bore 108. Accordingly, a secure and positive attachment or engagement is completed between first mating member 84 and second mating member 86.

Figure 9C:
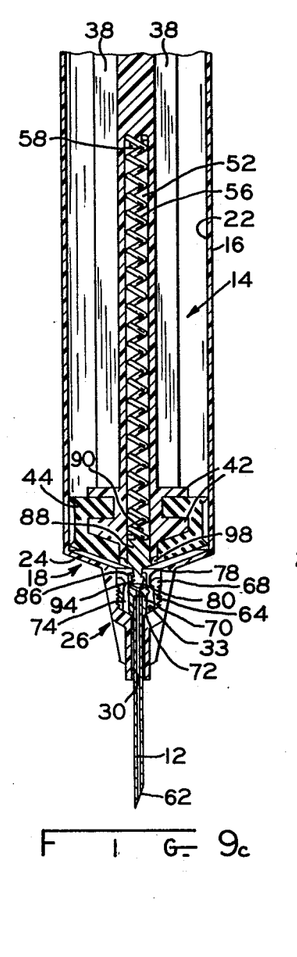

As the user of the hypodermic syringe 10 further pushes plunger 14 toward syringe closed end 18, needle 12 is detached from barrel 16 as shown in FIG. 9c. More specifically, the downward longitudinal force of plunger 14 causes sleeve 70 and needle 12 to be pushed downwardly with respect to plug 64, reaching the breaking point of the region of structural weakness 78 and, causing sleeve 70 to be broken away from upper ring portion 68 of plug 64. Thereafter, needle 12, sleeve 70 and plunger 14 all travel downwardly until seat 72 of sleeve 70 reaches and comes in contact with seat 33 of frusto-conical portion 26.

Figure 9D:
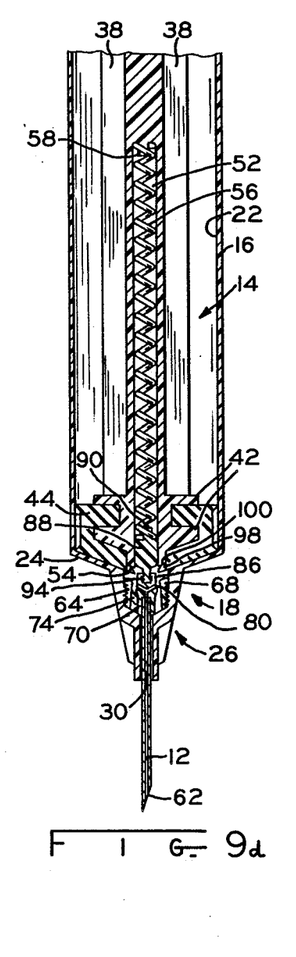
Figure 9E:
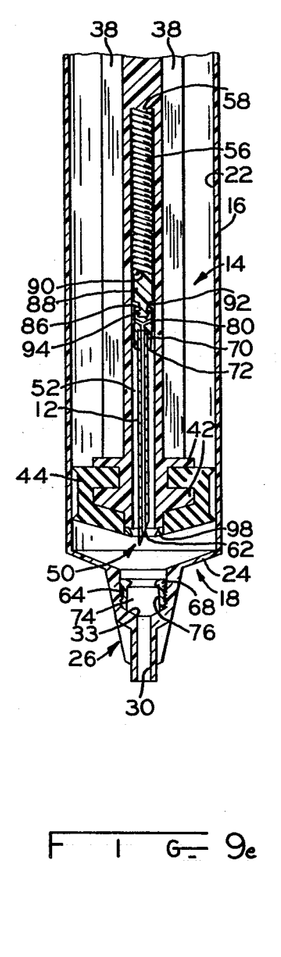

Thereafter, as shown in FIG. 9d, further downward movement of plunger 14 towards barrel closed end 18 causes seat 54 of plunger 14 to be pushed or urged downwardly against seat 100 of annular lip 98 of the first mating member 84. Accordingly, when a predetermined substantially longitudinal force is reached urging annular lip 98 downwardly with respect to first mating member 84, the breaking point of the area of structural weakness 102 is reached and annular lip 98 is detached or severed from the first mating member 84 as shown in FIG. 9d. Accordingly, because sleeve 70 converges or decreases in diameter downwardly, the maximum diameter of sleeve 70 is smaller than the inside diameter of the hole formed in annular lip 98 by the breaking away thereof from first mating member 84. Further, sleeve 70 is smaller in diameter than the diameter of duct 52 and, thus, after the severing of annular lip 98 from first mating member 84, needle 12, sleeve 70 and rod portion 88 of first mating member 84 are free to travel upwardly through now severed annular lip 98, hole 50 of plunger 14 and, to within duct 52 located in plunger 14.

Accordingly, immediately after annular lip 98 is broken away from first mating member 84, biasing means or spring 56 previously placed in tension during assembly, pulls or draws needle 12, sleeve 70 and rod portion 88 into duct 52 as shown in FIG. 9e. In this position, needle 12 and the sharp end 62 thereof are located within duct 52 of plunger 14 and out of the way so as to prevent accidental puncture with the contaminated needle 12. Furthermore, even if plunger 14 is taken out of barrel 16, accidental puncture is substantially prevented because the contaminated needle 12 is not exposed and, in fact, is fully retracted within duct 52 of plunger 14. The hypodermic syringe 10 has also been substantially rendered unusable in that a needle 12 is not attached to barrel 16 and plunger 14 has an opening or hole 50 therein. As can be appreciated, the hypodermic syringe 10 is substantially easy to operate and requires the pushing of plunger 14 only in one direction as is normally done with any syringe so as to cause needle 12 to be retracted after an injection and the possible contamination of needle 12.

It should be noted that the force required for the insertion of enlarged portion 94 to within bore 108 is smaller than the longitudinal force required for the breaking of the region of structural weakness 78 between sleeve 70 and plug 64. Furthermore, the longitudinal force required for the breaking of sleeve 70 away from plug 64 is smaller than the longitudinal force required for the breaking of the region of structural weakness 102 and the breaking away of annular lip 98 from rod portion 88 of the first mating member 84. In this fashion, and through these three different required longitudinal forces, a sequence of operation described hereinabove and shown in FIGS. 9a–9e, is possible so as to first cause the first mating member 84 to be attached to the second mating member 86, thereafter cause needle 12 and sleeve 70 to be detached from plug 64 and barrel 16 and, finally, cause annular lip 98 to be detached from rod portion 88 freeing the first mating member and causing spring 56 to pull or draw needle 12 to within duct 52 of plunger 14.

The various parts of the hypodermic syringe 10, such as barrel 16, plunger 14, and plug 64 are made of a plastic material of proper resiliency, while sealing member 44 is made of a substantially resilient rubber Needle 12 is made of stainless steel or other sufficiently stiff materials.

While the invention has been described as having specific embodiments, it will be understood that it is capable of further modifications. This application is, therefore, intended to cover any variations, uses, or adaptations of the invention following the general principles thereof and including such departures from the present disclosure as come within known or customary practice in the art to which this invention pertains and fall within the limits of the appended claims.

What is claimed is:

1. A hypodermic syringe comprising:
    a barrel having a closed end, an open end, and an interior surface;
    a plunger reciprocally received in said barrel through said open end in sealing engagement with said interior surface of said barrel and forming a chamber;
    a hollow needle detachably attached to said barrel at said closed end thereof providing communication between said chamber and the exterior of said barrel and wherethrough liquid in said chamber may be injected;
    means for forming a hole in said plunger for receiving said needle therethrough;
    biasing means connected to said plunger and attachable to said needle for drawing said needle through said plunger hole when said needle is detached from said barrel; and,
    wherein said needle is detached from said barrel by a predetermined substantially longitudinal force.

2. The hypodermic syringe of claim 1 further comprising attachment means between said biasing means and said needle for attaching said biasing means to said needle when said plunger approaches said barrel closed end.

3. The hypodermic syringe of claim 2 wherein said attachment means includes a first mating member connected to said biasing means and a second mating member connected to said needle and wherein said first and second mating members attach to one another when said plunger approaches said barrel closed end.

4. The hypodermic syringe of claim 3 wherein said first mating member includes a protrusion and said second mating member includes a bore therein for receiving said protrusion and further comprising catch means on said second mating member for catching and holding said protrusion in said bore when received therein.

5. The hypodermic syringe of claim 4 wherein said catch means includes an annular lip extending into said bore of said second mating member and said protrusion includes an enlarged portion, said annular lip retaining said enlarged portion in said bore when received therein.

6. The hypodermic syringe of claim 3 further comprising cavity means in said plunger and communicating with said hole for receiving said needle therein when detached from said barrel.

7. The hypodermic syringe of claim 6 wherein said biasing means is substantially in said cavity means.

8. The hypodermic syringe of claim 7 wherein said biasing means is a helical spring connected at one end to said plunger and at the other end to said first mating member.

9. The hypodermic syringe of claim 7 wherein said first mating means is detachably attached to said plunger and detaches from said plunger by a predetermined substantially longitudinal force.

10. The hypodermic syringe of claim 9 wherein said first mating member includes a detachably attached annular lip larger than said plunger hole and preventing said first mating member from being drawn through said plunger hole by said biasing means, said lip being detached from said first mating member by said predetermined substantially longitudinal force and detaching said first mating member from said plunger.

11. The hypodermic syringe of claim 9 wherein said first mating member is integrally formed with said plunger and is adapted to be detached therefrom by said predetermined substantially longitudinal force.

12. The hypodermic syringe of claim 9 wherein said first mating member is situated substantially in said cavity means near said hole and includes an annular groove and an annular ring is connected to said plunger and extends into said cavity means and in said annular groove and wherein said predetermined substantially longitudinal force forces said ring out of said annular groove and detaches said first mating member from said plunger.

13. The hypodermic syringe of claim 1 further comprising cavity means in said plunger and communicating with said hole for receiving said needle therein when detached from said barrel.

14. The hypodermic syringe of claim 13 wherein said biasing means is substantially in said cavity means.

15. The hypodermic syringe of claim 14 wherein said biasing means is a helical spring.

16. The hypodermic syringe of claim 1 wherein said biasing means is a helical spring.

17. The hypodermic syringe of claim 1 wherein said needle is detachably attached to a plug that is threadably connected to said barrel.

18. The hypodermic syringe of claim 1 wherein said needle is attached to said barrel through a region of structural weakness, said needle detaching from said barrel substantially at said region of structural weakness.

19. The hypodermic syringe of claim 18 wherein said needle is detachably attached to a plug that is threadably connected to said barrel, said region of structural weakness located on said plug.

20. The hypodermic needle of claim 1 further comprising a frusto-conical portion having a bore therethrough larger in diameter than said needle, said frusto-conical portion connected to said barrel closed end and said needle received through said frusto-conical portion bore whereby said needle is supported.

21. A hypodermic syringe comprising:
    a barrel having a closed end, an open end, and an interior surface;
    a plunger reciprocally received in said barrel through said open end in sealing engagement with said interior surface of said barrel and forming a chamber;
    a hollow needle detachably attached to said barrel at said closed end thereof providing communication between said chamber and the exterior of said barrel and wherethrough liquid in said chamber may be injected;
    means for forming a hole in said plunger for receiving said needle therethrough;

cavity means in said plunger and communicating with said hole for receiving said needle therein when detached from said barrel;

biasing means connected to said plunger for drawing said needle through said plunger hole and into said cavity means when said needle is detached from said barrel;

attachment means connected to said biasing means and located between said biasing means and said needle for attaching said biasing means to said needle when said plunger approaches said barrel closed end; and, wherein said needle is detached from said barrel by a predetermined substantially longitudinal force.

22. The hypodermic syringe of claim 21 wherein said attachment means includes a first mating member connected to said biasing means and a second mating member connected to said needle and wherein said first and second mating members attach to one another when said plunger approaches said barrel closed end.

23. The hypodermic syringe of claim 22 wherein said first mating member is detachably attached to said plunger and detaches from said plunger by a predetermined substantially longitudinal force.

24. The hypodermic syringe of claim 22 wherein said first mating member includes a detachably attached annular lip larger than said plunger hole and preventing said first mating member from being drawn through said plunger hole by said biasing means, said lip being detached from said first mating member by a predetermined substantially longitudinal force whereby said first mating member may be drawn through said plunger hole and into said cavity means.

25. The hypodermic syringe of claim 23 wherein said biasing means is a helical spring connected at one end to said plunger and at the other end to said attachment means.

26. The hypodermic syringe needle of claim 23 wherein said needle is attached to said barrel through a region of structural weakness, said needle detaching from said barrel substantially at said region of structural weakness.

27. A hypodermic syringe comprising:
a barrel having a closed end, an open end, and an interior surface;
a plunger reciprocally received in said barrel through said open end in sealing engagement with said interior surface of said barrel and forming a chamber;
a hollow needle detachably attached to said barrel at said closed end thereof providing communication between said chamber and the exterior of said barrel and wherethrough liquid in said chamber may be injected;
means for forming a hole in said plunger for receiving said needle therethrough;
biasing means connected to said plunger and attachable to said needle for drawing said needle through said plunger hole when said needle is detached from said barrel;
attachment means between said biasing means and said needle for attaching said biasing means to said needle when said plunger approaches said barrel closed end;
wherein said attachment means includes a first mating member connected to said biasing means and a second mating member connected to said needle and wherein said first and second mating members attach to one another when said plunger approaches said barrel closed end;
cavity means in said plunger and communicating with said hole for receiving said needle therein when detached from said barrel;
wherein said biasing means is substantially in said cavity means; and,
wherein said first mating means is detachably attached to said plunger and detaches from said plunger by a predetermined substantially longitudinal force.

28. The hypodermic syringe of claim 27 wherein said first mating member includes a detachably attached annular lip larger than said plunger hole and preventing said first mating member from being drawn through said plunger hole by said biasing means, said lip being detached from said first mating member by said predetermined substantially longitudinal force and detaching said first mating member from said plunger.

29. The hypodermic syringe of claim 27 wherein said first mating member is integrally formed with said plunger and is adapted to be detached therefrom by said predetermined substantially longitudinal force.

30. The hypodermic syringe of claim 27 wherein said first mating member is situated substantially in said cavity means near said hole and includes an annular groove and an annular ring is connected to said plunger and extends into said cavity means and in said annular groove and wherein said predetermined substantially longitudinal force forces said ring out of said annular groove and detaches said first mating member from said plunger.

31. A hypodermic syringe comprising:
a barrel having a closed end, an open end, and an interior surface;
a plunger reciprocally received in said barrel through said open end in sealing engagement with said interior surface of said barrel and forming a chamber;
a hollow needle detachably attached to said barrel at said closed end thereof providing communication between said chamber and the exterior of said barrel and wherethrough liquid in said chamber may be injected;
means for forming a hole in said plunger for receiving said needle therethrough;
biasing means connected to said plunger and attachable to said needle for drawing said needle through said plunger hole when said needle is detached from said barrel; and,
wherein said needle is attached to said barrel through a region of structural weakness, said needle detaching from said barrel substantially at said region of structural weakness.

32. The hypodermic syringe of claim 31 wherein said needle is detachably attached to a plug that is threadedly connected to said barrel, said region of structural weakness located on said plug.

33. A hypodermic syringe comprising:
a barrel having a closed end, an open end, and an interior surface;
a plunger reciprocally received in said barrel through said open end in sealing engagement with said interior surface of said barrel and forming a chamber;
a hollow needle detachably attached to said barrel at said closed end thereof providing communication between said chamber and the exterior of said barrel and wherethrough liquid in said chamber may be injected;

means for forming a hole in said plunger for receiving said needle therethrough;

cavity means in said plunger and communicating with said hole for receiving said needle therein when detached from said barrel;

biasing means connected to said plunger for drawing said needle through said plunger hole and into said cavity means when said needle is detached from said barrel;

attachment means connected to said biasing means and located between said biasing means and said needle for attaching said biasing means to said needle when said plunger approaches said barrel closed end;

wherein said attachment means includes a first mating member connected to said biasing means and a second mating member connected to said needle and wherein said first and second mating members attach to one another when said plunger approaches said barrel closed end; and, wherein said first mating member includes a detachably attached annular lip larger than said plunger hole and preventing said first mating member from being drawn through said plunger hole by said biasing means, said lip being detached from said first mating member by a predetermined substantially longitudinal force whereby said first mating member may be drawn through said plunger hole and into said cavity means.

* * * * *